(12) United States Patent
Awano et al.

(10) Patent No.: US 7,887,684 B2
(45) Date of Patent: Feb. 15, 2011

(54) LAMINATION-TYPE GAS SENSOR ELEMENT AND GAS SENSOR

(75) Inventors: Shinya Awano, Kasugai (JP); Keisuke Makino, Mizuho (JP); Yoshiaki Kuroki, Inuyama (JP); Takao Kojima, Nagoya (JP); Masashi Ando, Inazawa (JP)

(73) Assignee: NGK Spark Plug Co., Ltd., Aichi (JP)

( * ) Notice: Subject to any disclaimer, the term of this patent is extended or adjusted under 35 U.S.C. 154(b) by 974 days.

(21) Appl. No.: 11/174,583

(22) Filed: Jul. 6, 2005

(65) Prior Publication Data

US 2007/0007136 A1 Jan. 11, 2007

(51) Int. Cl.
*G01N 27/407* (2006.01)

(52) U.S. Cl. .................. 204/426; 204/424; 204/428; 204/429

(58) Field of Classification Search .................. None
See application file for complete search history.

(56) References Cited

U.S. PATENT DOCUMENTS

| | | | |
|---|---|---|---|
| 5,419,828 | A | 5/1995 | Nakano et al. |
| 5,935,399 | A * | 8/1999 | Tanaka et al. ............ 204/424 |
| 6,196,049 | B1 | 3/2001 | Schneider |
| 7,156,967 | B2 * | 1/2007 | Hotta et al. .............. 204/429 |
| 7,160,422 | B2 | 1/2007 | Imamura et al. |
| 2003/0146093 | A1 | 8/2003 | Akiyama et al. |
| 2003/0159928 | A1 | 8/2003 | Kojima et al. |
| 2003/0188969 | A1 | 10/2003 | Imamura et al. |

FOREIGN PATENT DOCUMENTS

| | | |
|---|---|---|
| JP | 7120429 A | 5/1995 |
| JP | 8-193971 | 7/1996 |
| JP | 10-104184 | 4/1998 |
| JP | 11-223616 A | 8/1999 |
| JP | 2001-281210 | 10/2001 |
| JP | 2002340845 A | 11/2002 |
| JP | 2003247969 A | 9/2003 |
| JP | 2003-279527 | 10/2003 |
| JP | 2003-279529 | 10/2003 |
| JP | 2003-279529 A | 10/2003 |
| JP | 2003-322632 | 11/2003 |
| JP | 2003-322632 A | 11/2003 |
| JP | 2004003963 A | 1/2004 |

* cited by examiner

*Primary Examiner*—Nam X Nguyen
*Assistant Examiner*—Kourtney R Salzman
(74) *Attorney, Agent, or Firm*—Sughrue Mion, PLLC

(57) ABSTRACT

A gas sensor element having an element body, the element body including: a ceramic heater having ceramic layers and a heater element embedded in the ceramic layers; and a solid electrolyte layer including a detection section covered by a pair of electrodes, the solid electrolyte layer being laminated together with the ceramic heater. Furthermore, the element body has a width at a front portion including the detection section smaller than at a rear portion, and at least both side edge faces of the front portion of the element body are covered with a porous layer.

9 Claims, 9 Drawing Sheets

LAMINATION-TYPE GAS SENSOR ELEMENT AND GAS SENSOR

BACKGROUND OF THE INVENTION

1. Field of the Invention

This invention relates to a lamination-type gas sensor element and a gas sensor, and more particularly to a lamination-type gas sensor element which is less susceptible to damage upon contact of an element body with a water drop, and which provides for early activation of a detection section by heating with a ceramic heater. The invention also relates to a gas sensor including the lamination-type gas sensor element.

2. Description of the Related Art

A gas sensor including a lamination-type gas sensor element is known as one kind of gas sensor capable of detecting oxygen, carbon monoxide, various hydrocarbons, nitrogen oxide (NOx), etc., in exhaust gas emitted from an internal-combustion engine or measuring the concentration thereof. The lamination-type gas sensor element for an oxygen sensor (lamination-type oxygen sensor element) has an element body obtained by laminating 1) a ceramic heater including ceramic layers and a heater element embedded in the ceramic layers, and 2) a solid electrolyte layer having a pair of electrodes sandwiching a portion thereof. The portion of the solid electrolyte layer sandwiched between the paired electrodes functions as an oxygen concentration cell and becomes a detection section for detecting the oxygen concentration. Such a lamination-type oxygen sensor element is not activated until the solid electrolyte layer reaches a predetermined high temperature. Therefore, a technique of heating the solid electrolyte layer (detection section) with a heater element from the start time of an internal-combustion engine to activate the sensor and secure early oxygen concentration detection has been proposed.

On the other hand, condensed water is usually deposited on an exhaust pipe wall under conditions where the temperature in the exhaust pipe (the temperature of the wall of the exhaust pipe) is low at the cold start time of an internal-combustion engine. Thus, if the heater element is energized for heating the detection section to a high temperature, the lamination-type gas sensor element (element body) may be damaged by thermal shock caused by water condensation. Thus, hitherto, the detection section of the gas sensor element has been protected by a metal protector having a vent hole. However, even if such a protector is used, water may enter the element through the vent hole of the protector, and damage to the element body, such as cracks in the element body, cannot be sufficiently prevented. In view of securing sufficient exhaust gas flow and sufficient gas detection performance, the vent hole cannot be made small enough to eliminate water intrusion.

To solve the above problem, a lamination-type gas sensor element has been proposed where the part of an element body which can be damaged is covered with a porous layer for suppressing direct contact of a water drop, etc., with the element body. See, for example, JP-A-2001-281210. In the gas sensor element described in JP-A-2001-281210, if a water drop is deposited on the porous layer, the water drop can be evaporated by heating the gas sensor element before it penetrates the detection section. As a result, since a large thermal shock is unlikely to reach the element body, damage to the element body can be suppressed.

3. Problems to be Solved by the Invention

However, there is a possibility that the structure described in JP-A-2001-281210 will not be able to meet the recent demand of sufficiently early activation of the detection section. Namely, the element body in JP-A-2001-281210 must be formed with a porous layer sufficiently thick to impart water resistance. However, as the porous layer is made thicker, the volume surrounding the detection section containing the porous layer increases. Consequently it takes a longer time to heat the detection section to the activation temperature using a ceramic heater. Also, each corner of the element body forming the gas sensor element is prone to damage due to thermal shock, etc., and requires sufficient damage prevention measures, but the gas sensor element described in JP-A-2001-281210 does not address this problem.

SUMMARY OF THE INVENTION

It is therefore an object of the invention to provide a lamination-type gas sensor element which suppresses damage to an element body caused by deposition of a water drop, etc., particularly damage to a detection section and its periphery, and which promotes early activation of the detection section, and to provide a gas sensor including the lamination-type gas sensor element.

To this end, the invention provides a lamination-type gas sensor element comprising an element body having a front portion including two side faces and a rear portion, the element body including: a ceramic heater comprising ceramic layers and a heater element embedded in said ceramic layers; and a solid electrolyte layer comprising a detection section. The detection section is covered by a pair of electrodes, and the solid electrolyte layer is laminated with said ceramic heater. Furthermore, the front portion of the element body including the detection section has a smaller width than the rear portion of the element body, and at least both side faces of the front portion of the element body are covered with a porous layer.

According to the lamination-type gas sensor element of the invention, at least both side faces (i.e., opposing side edge faces) of the front portion of the element body are covered with a porous layer. Both side faces of the front portion of the element body, at which the lamination interface is exposed, are also exposed to the gas to be measured. Thus, if water drops contact one or both of the side faces, the element body is likely to be damaged. In the invention, however, both side faces are covered with a porous layer, to prevent flying water drops from depositing or condensing directly on the side faces.

Water drops that are deposited on the porous layer slowly percolate through a large number of pores of the porous layer. Thus, water drops can be dispersed before reaching the element body positioned inside the porous layer. Consequently, the reduced temperature gradient of the element body can effectively suppress thermal shock. Therefore, damage to the element body (in the proximity of the detection section) caused by deposition of a water drop can be prevented. When the lamination-type gas sensor element is operated, it is heated to a high temperature by the heater element and thus water drops percolating through the porous layer are evaporated by the heat of the heated gas sensor element. It is also possible to employ additional measures to keep water drops away from the element body in the first instance.

In the lamination-type gas sensor element of the invention, the width of the front portion of the element body covered with the porous layer is smaller than the width of the rear portion of the element body. Thus, the total volume of both the front portion and a porous layer of considerable thickness covering the front portion can be reduced relative to a conventional element body including a front portion having the same width as the rear portion and being covered with a porous layer. Therefore, due to the reduced total volume of the front portion of the element body and the porous layer, the front portion (detection section) can be heated and thus activated faster, despite employing a porous layer thicker than that of a conventional element body where the front portion has the same width as the rear portion. As used herein, the "width" of the element body is measured in a direction orthogonal to a longitudinal direction and a laminating (thickness) direction.

The composition of the above-noted "ceramic layers" are not particularly limited so long as they form a ceramic fired body. Preferably, the ceramic layers are made of alumina, spinel, mullite, etc., and have insulating properties that are maintained even at high temperatures. Only one kind of ceramic may be used or two or more kinds can be used in combination.

The material of the above-noted "heater element" is not particularly limited. For example, the heater element may be made of a noble metal, tungsten, or molybdenum. Pt, Au, Pd, Ir, Ru and Rh are examples of the noble metal. Only one kind may be used or two or more can also be used together. Also, an alloy may be used if two or more kinds are used. Further, among the noble metals, preferably Pt is mainly used in consideration of heat resistance, oxidation resistance, etc. In addition to the noble metal, the heater element can contain a ceramic component. The kind of ceramic component is not particularly limited. Preferably, the ceramic component is the same as the ceramic component forming the ceramic layers which contact the heater element to provide enhanced fixing strength.

The above-noted "solid electrolyte layer" can generally be formed of zirconia ($ZrO_2$) having oxygen ion conductivity. The electrolyte layer can contain the same component as the main ceramic component of the ceramic layers. The content of the ceramic component in the solid electrolyte layer can be 10% by mass to 80% by mass, preferably 20% by mass to 70% by mass based on the solid electrolyte layer taken as 100% by mass. Accordingly, stress caused by a difference in thermal expansion between the ceramic layers and the solid electrolyte layer can be relieved.

The material of the above-noted "electrode" disposed on the solid electrolyte layer is not limited, but a noble metal is preferred. Pt is particularly preferred. The electrode may be formed of two or more kinds of metals; and an alloy may be used if the electrode is made of two or more kinds of metal. For example, the electrode may consist essentially of Pt with Au, Ag, Pd, Ir, Ru, Rh, etc., contained therein, and an alloy of Pt and any other noble metal may be used. Particularly, Pt is effectively used together with Rh which is capable of suppressing volatilization of Pt at high temperatures.

In the lamination-type gas sensor element described above, the rear portion includes a plurality of terminal electrodes on an outer surface thereof, the terminal electrodes being electrically connected to the pair of electrodes and to the heater element. In a preferred embodiment, the element body further includes an intermediate part arranged between the front portion and the rear portion having a width which increases gradually from a side of the front portion to a side of the rear portion. Furthermore, the porous layer covers a side face (i.e., side edge face) of a boundary part between the front part and the intermediate part.

An example of a configuration where the width of the front portion containing the detection section of the element body is made smaller than the width of the rear portion is a configuration where an intermediate part having a width which gradually increases from the front portion side of the element body to the rear portion side of the element body is arranged between the front portion and the rear portion. By providing the intermediate part, the element body can have a front portion of reduced width while maintaining its strength. If the porous layer is arranged so as not to cover the side face of the boundary part, the boundary part is directly exposed to water drops which can damage the boundary part.

In the lamination-type gas sensor element of the invention, the porous layer covers the side edge faces of the front portion up to the side edge face of the boundary part joining the intermediate part and the front portion. Accordingly, the boundary part is spared from damage. In a lamination-type gas sensor element configured to have an intermediate part, preferably the porous layer at the boundary part is made thicker than at the side face of the front portion. Thus, the boundary part, which is the weakest portion of the element body, is protected by a thicker porous layer. Because the porous layer is formed so as to have such a thickness relationship, damage to the element body can be further suppressed.

Further, in the lamination-type gas sensor element described above, the total dimension of the width of the front portion of the element body and the thickness of the porous layer covering both side faces of the front portion is equal to or smaller than the maximum width of the rear portion of the element body.

The lamination-type gas sensor element is thus formed by appropriately adjusting the width of the front portion and the thickness of the porous layer so that the total width of the front portion of the element body and the thickness of the porous layer covering both side faces of the front portion is equal to or smaller than the maximum width of the rear portion of the element body. As a result, the front portion (namely, the detection section) can be promptly heated by the heater element (ceramic heater) so as to promote early activation of the detection section.

Further, in the lamination-type gas sensor element described above, the relationship $A \times 0.60 < B < A \times 0.98$ is preferably satisfied where A is the width of the front portion of the element body (in mm units) and B is the maximum width of the part of the heater element positioned at the front portion (in units of mm).

The lamination-type gas sensor element is configured so that the maximum width of the part of the heater element positioned at the front portion satisfies the above relationship based on the width of the front portion of the element body. As such, the front portion (namely, the detection section) can be promptly heated by the heater element which promotes early activation of the detection section.

Further, in the lamination-type gas sensor element described above, the porous layer may cover surrounding areas including the entire peripheral area of the front portion, and preferably includes a first porous layer covering at least both side edge faces of the front portion of the element body and a second porous layer covering the first porous layer.

By configuration the porous layer in this manner, damage caused by water covering or pouring on the element body can be suppressed more efficiently. That is, in the lamination-type gas sensor element of the invention, the cross-sectional shape along the laminating direction of the element body is a plate shape roughly in the form of a quadrangle and thus the element body has corners. If a water drop is deposited on any of the corners, thermal stress easily concentrates on the corner and a crack tends to easily occur in the element body. Thus the porous layer covering the surrounding areas of the front portion prevents a water drop from depositing directly on the corner of the element body, and damage to the element body caused by water covering or pouring water thereupon can be effectively suppressed. If the porous layer is a single layer, there is a limit to increasing its thickness. Thus, the second porous layer is provided as described above, whereby the thickness of the porous layer on both side faces of the front portion can be easily controlled. Furthermore, such multi-layer structure of the porous layer improves design flexibility.

Further, in the lamination-type gas sensor element described above, the porous layer may be formed so as to cover surrounding areas of the front portion containing both side edge faces, and the thickness of the porous layer extending from a corner of the element body may be 20 μm or more.

Thus, while the porous layer covers the surrounding areas of the front portion of the element body, the thickness of the porous layer extending from the corner of the element body is set to 20 μm or more. As such, damage to the element body caused by water covering or pouring thereon can be effectively prevented. To more effectively prevent water damage, preferably the thickness of the porous layer extending from the corner of the element body is set to 30 μm or more (more preferably, 50 μm or more). The expression "the thickness of the porous layer extending from the corner of the element body is set to 20 μm or more" as used herein means that in cross section along the laminating (thickness) direction of the element body, the porous layer occupies a virtual circle measuring 20 μm in diameter between the corner of the element body and the outer surface of the porous layer. The term "corner" as used herein refers to the ridge part joining one of the upper and lower faces extending in the length direction, of the plate-like element body and one of the side faces. Such a ridge part can be configured not only as a peak but also as a curved surface part (e.g., chamfered face) joining the two faces as a round shape, for example.

Further, in the lamination-type gas sensor element described above, preferably the porous layer has a porosity ranging from 15% to 65%. If the porosity is less than 15%, the ability of the porous layer for slowly percolating water drops while dispersing the same may be insufficient. If the porosity exceeds 65%, the percolating degree of water drops, etc., in the porous layer becomes high and water drops, etc., easily come into contact with the element body. Thus, the effect of suppressing damage to the element body caused by water covering or pouring thereon may be insufficient. The term "porosity" as used herein is determined by analyzing the cross section of the porous layer under a scanning electron microscope and finding the pore area percentage per unit area (%).

According to another aspect of the invention, a gas sensor is provided including the above-described lamination-type gas sensor element and a cylindrical housing surrounding the circumferential direction of the lamination-type gas sensor element, wherein the detection section protrudes from the tip of the cylindrical housing.

The gas sensor of the invention is formed using the lamination-type gas sensor element including an element body resistant to damage due to deposition of a water drop, etc. Thus, the gas sensor has excellent water resistance (water proofness) and is highly reliable. Further, since the gas sensor of the invention is formed using the lamination-type gas sensor element which allows for early activation of the detection section, the gas sensor can provide early gas detection and can also comply with recent rigorous emission control standards.

DESCRIPTION OF REFERENCE NUMERALS

Figure 1:
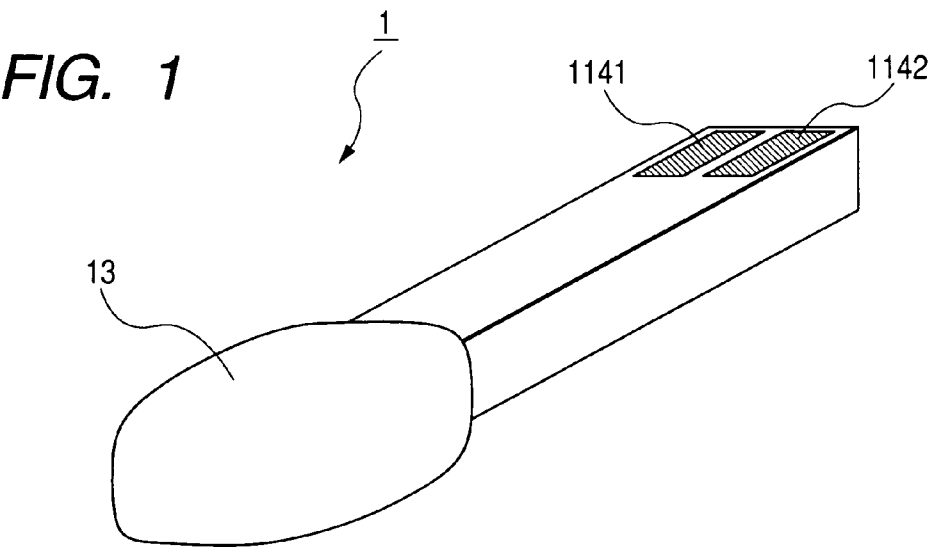
FIG. 1 is a perspective view of a lamination-type oxygen sensor element of an embodiment of the invention.

Reference numerals used to identify various structural elements in the drawings include the following.
1, 20: lamination-type gas sensor element (lamination-type oxygen sensor element)
11: detection element
111: solid electrolyte layer
112: detection electrode
113: reference electrode
1141, 1142: signal taking-out terminal pad
116: electrode protection layer
12: ceramic heater
121: heater element
122: first alumina layer
123: second alumina layer
1241, 1242: heater energization terminal pad
13: porous protection layer (porous layer)
131: first porous layer
132: second porous layer
2: through hole
3: mold release agent
4: mask,
5, 50: gas sensor (oxygen sensor)
51: outer cylinder
511: grommet
52: housing
101: front portion
103: intermediate part
105: rear portion
107: boundary part
61: ceramic holder
65: holder side engagement part

DETAILED DESCRIPTION OF THE INVENTION

The invention will next be described by reference to the drawings, to include an embodiment and a modified example. However, the present invention should not be construed as being limited thereto.

Embodiment

Figure 10:
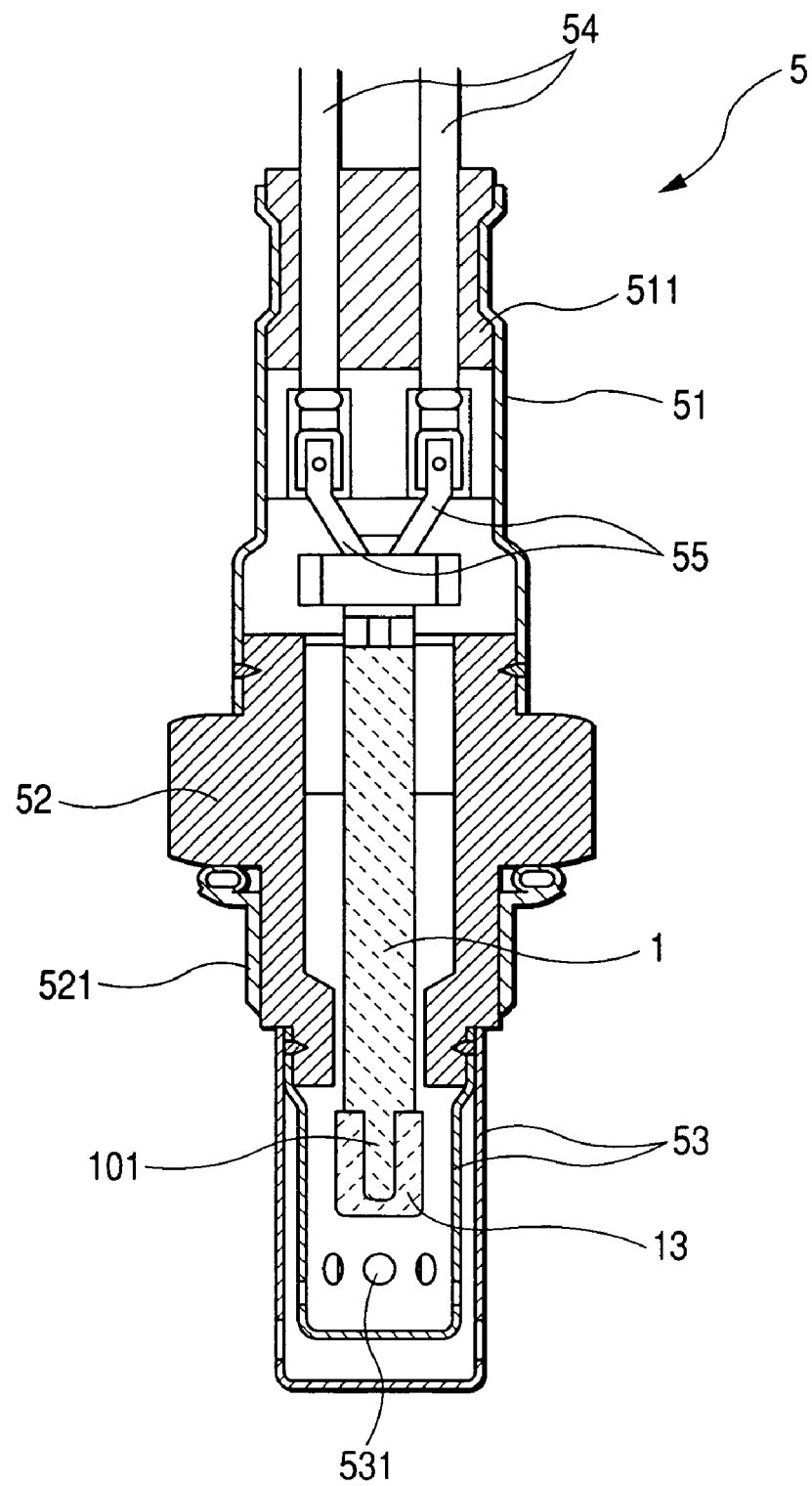
FIG. 10 is a general schematic sectional view showing the structure of a gas sensor (oxygen sensor) of an embodiment of the invention.

First, a gas sensor 5 according to an embodiment of the invention will be discussed with reference to FIG. 10. As shown in FIG. 10, the gas sensor 5 of the embodiment includes a built-in lamination-type gas sensor element 1 attached to an exhaust pipe of an internal-combustion engine. The gas sensor is used to measure the oxygen concentration in exhaust gas. The lamination-type gas sensor element 1 is inserted into the gas sensor 5 within cylindrical housing 52. The detection section of the gas sensor element 1 protrudes from the tip end of the cylindrical housing 52. The lamination-type gas sensor element 1 is sealed with glass in the housing 52, whereby it is held at a predetermined position of the housing 52. A protector 53 having a dual structure is fixedly secured to the outer periphery of a tip end of the housing 52 so as to shield the detection section formed at a tip end of the lamination-type gas sensor element 1. The protector 53 is formed at the tip end of the cylindrical housing 52 and on a side peripheral surface with a vent hole 531 for introducing exhaust gas flowing through the exhaust pipe into the interior of the housing 52. Thus, the tip end of the detection section projecting from the tip end of the housing 52 in the lamination-type gas sensor element 1 is exposed to the detected gas (exhaust gas). A porous protection layer 13 (described below) covers a front portion 101 containing the detection section of the lamination-type gas sensor element 1 on both side faces and the tip end face (i.e., the edge face perpendicular to the lengthwise direction) below so as to cover the side and end faces.

Further, the rear portion of the housing 52 is inserted into the inside of the front portion of an outer cylinder 51 and preferably laser welded over the entire circumference in the overlapping part of the rear portion of the housing 52 and the front portion of the outer cylinder 51 to fixedly secure the housing 52 and the outer cylinder 51. The housing 52 is formed in an outer peripheral part with a threaded part 521 for attaching the gas sensor 5 to the exhaust pipe. Further, the gas sensor 5 has four lead wires 54 (only two lead wires are shown in FIG. 10) drawn from inside the outer cylinder 51 to the outside. The lead wires 54 are electrically connected to the lamination-type gas sensor element 1 through relay terminals 55 housed in the outer cylinder 51. Specifically, the lead wires 54 are electrically connected to a detection electrode 112 and a reference electrode 113 of a detection element 11 (described below) and separately to a positive electrode and a negative electrode of a heater element 121 of a ceramic heater 12. The lead wires 54 are passed through lead wire insertion holes of a grommet 511 fitted into the rear end side of the outer cylinder 51 and extending to the outside, and are electrically connected to an external circuit.

Next, the lamination-type gas sensor element 1 of the main part of the invention will be discussed in detail. The lamination-type gas sensor element 1 of the embodiment is provided for detecting the oxygen concentration in exhaust gas and is also called a lamination-type oxygen sensor element.

[1] Structure of Lamination-type Gas Sensor Element 1

The structure of the lamination-type gas sensor element 1 will be discussed with reference to FIGS. 1 to 3. FIG. 3 is an exploded perspective view of the lamination-type gas sensor element 1. The lamination-type gas sensor element 1 is obtained by laminating the detection element 11 and the ceramic heater 12. In FIG. 3, the porous protection layer 13 is not shown.

The detection element 11 includes a solid electrolyte layer 111 containing 60% by mass of partially stabilized zirconia having oxygen ion conductivity with a predetermined amount of yttria dissolved therein as a stabilizer and 40% by mass of alumina. The detection electrode 112 is formed on the surface of the tip end of the solid electrolyte layer 111 and the reference electrode 113 is formed at a position corresponding to the detection electrode 112 on the back of the solid electrolyte layer 111. A detection electrode lead part 1121 and a reference electrode lead part 1131 extend from the detection electrode 112 and the reference electrode 113, respectively. In the embodiment, the portion of the solid electrolyte layer 111 sandwiched between the detection electrode 112 and the reference electrode 113 corresponds to the "detection section."

The end of the detection electrode lead part 1121 is connected to a signal output terminal pad 1142 for connecting to the relay terminal 55 (see FIG. 10) by a through hole conductor 1152 piercing a protective insulating layer 115. Further, the end of the reference electrode lead part 1131 is connected to a signal output terminal pad 1141 for connecting to the relay terminal 55 by a through hole conductor 1111 piercing the solid electrolyte layer 111 and a through hole conductor 1151 piercing the protective insulating layer 115 via terminal pad 1143. To prevent poisoning of the detection electrode 112, an electrode protection layer 116 made of a porous substance is formed on the surface of the solid electrolyte layer 111 on which the detection electrode 112 is formed.

The ceramic heater 12 has a heater element 121 made of platinum and the heater element 121 is sandwiched between a first alumina layer 122 and a second alumina layer 123 each consisting essentially of alumina having excellent insulation properties. Lead parts 1211 extend from the heater element 121 and the ends of the lead parts 1211 are electrically connected to heater energization terminal pads 1241 and 1242 by two through hole conductors 1221 and 1222 piecing the first alumina layer 122. The heater energization terminal pads 1241 and 1242 are connected to the relay terminals 55 (see FIG. 10).

Figure 2:
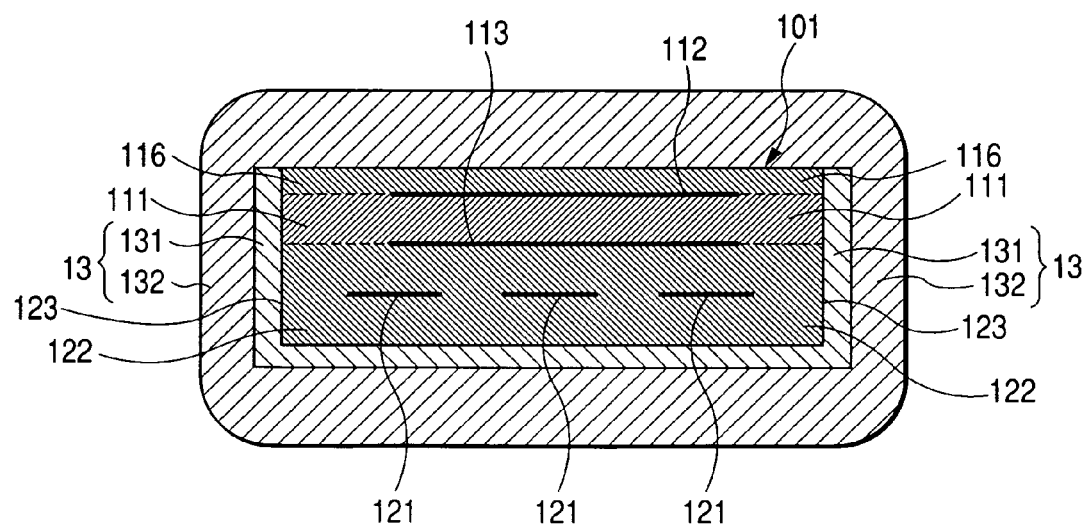
FIG. 2 is a transverse section of the lamination-type oxygen sensor element of FIG. 1 formed with a porous protection layer including a first porous layer and a second porous layer at the front portion of the sensor element containing a detection section.
Figure 3:
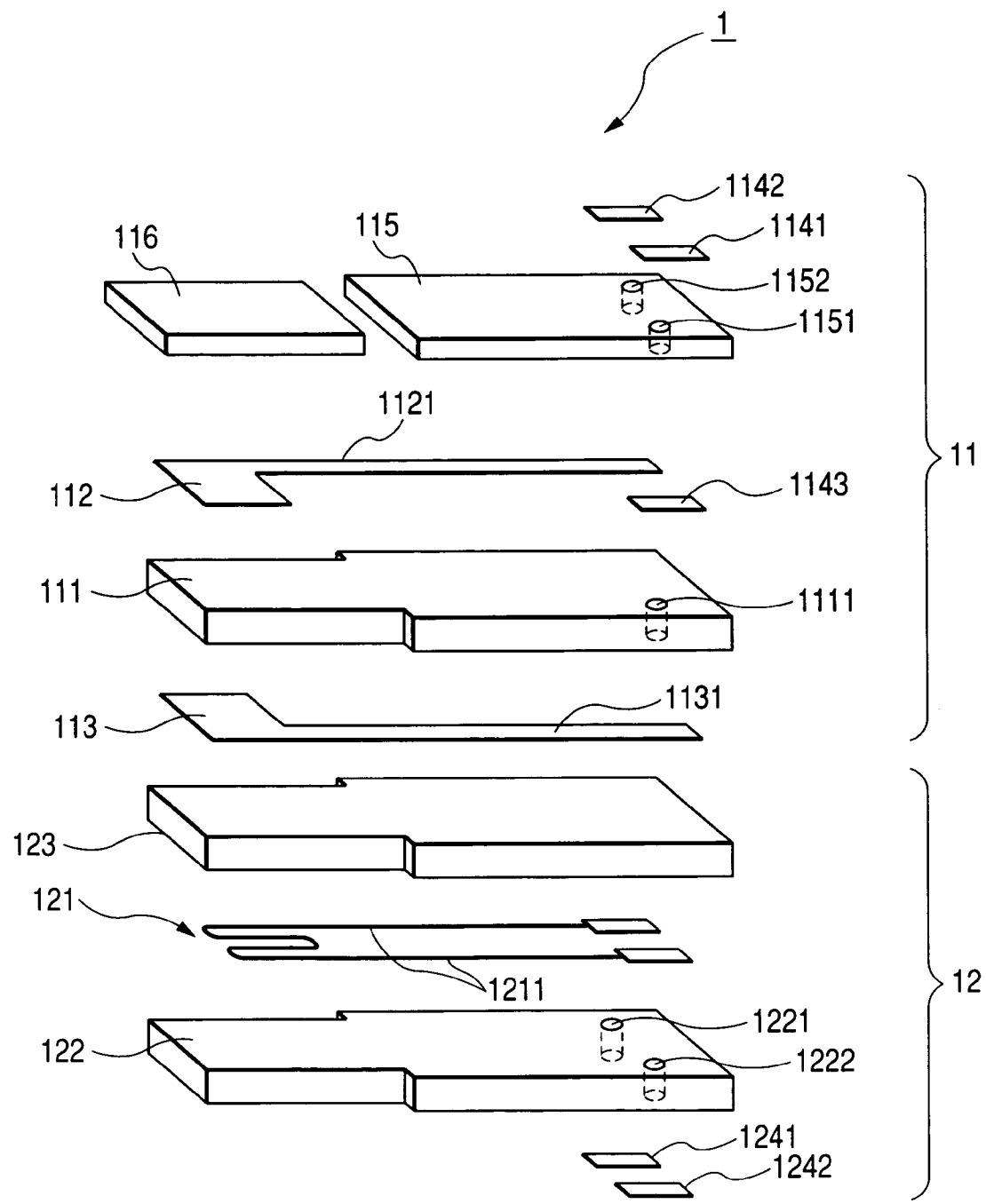
FIG. 3 is an exploded perspective view of the lamination-type oxygen sensor element of an embodiment of the invention.

Further, when a cross section of the lamination-type gas sensor element 1 is taken along the laminating direction so as to contain the detection section, the entire periphery of the element body made of the laminated body of the detection element 11 and the ceramic heater 12 are covered with the porous protection layer 13 made of a first porous layer 131 and a second porous layer 132, as shown in FIG. 2. The tip end face of the element body of the lamination-type gas sensor element 1 is also covered with the porous protection layer 13, as shown in FIG. 10. The thickness of the porous protection layer 13 is 200 μm at a corner of the element body.

The dimensions of the portion of the lamination-type gas sensor element 1 of the embodiment except the porous protection layer 13 are as follows: The length (the dimension along the length direction) is 40 mm, the width (the dimension in the direction orthogonal to the length direction and the laminating direction) is 3 mm, and the thickness (the dimension along the laminating direction) is 2 mm. The width of the front portion 101 containing the detection section of the element body is smaller than the width of the rear portion, as slightly exaggerated for purposes of illustration in FIG. 3. Specifically, the width of the front portion 101 of the element body is 2.7 mm and the width of the rear portion is 3.0 mm; in the portion corresponding to the detection section, the width is reduced by 300 μm (150 μm on each side in the width direction). The porous protection layer 13 is formed so as to cover at least both side edges of the front portion 101 having a width smaller than the rear portion (see FIG. 10, where the porous protection layer 13 covers the side edge faces and the tip end face, but not the entire periphery of the front portion 101). In the embodiment, the width of the heater element 121, etc., is appropriately adjusted so that A×0.90=B where A is the width of the front portion 101 (in units of mm) and B is the maximum width of the part of the heater element 121 positioned at the front portion 101 (in units of mm).

[2] Manufacturing the Lamination-Type Gas Sensor Element

Next, a method of manufacturing the lamination-type gas sensor element 1 according to the embodiment will be described.

In manufacturing the lamination-type gas sensor element 1, a through hole forming process, a filling process, a cutting process, and a firing process are executed in this order after an unfired laminated sheet body is prepared. After the firing process, a coating process is executed, thereby forming a second porous layer 132.

(1) Preparation of Unfired Detection Element

An unfired sheet which will become a solid electrolyte layer 111 was prepared using a slurry provided by wet mixing 60% by mass of zirconia powder partially stabilized with yttria and 40% by mass of alumina powder with an organic binder, an organic solvent, etc. The unfired sheet was sized to accommodate 32 unfired gas sensor elements for dicing, and was formed with as many through holes as the 32 elements at predetermined positions. Furthermore, the 32 unfired gas sensor elements were separated by a predetermined spacing (allowance) from one another. Next, a predetermined pattern of conductive paste consisting essentially of platinum was printed at a predetermined place at the right side and back of the unfired sheet and dried to form an electrode pattern which will become a detection electrode 112, a reference electrode 113, lead parts 1121 and 1131 and an unfired conductor which will become a through hole conductor 1111.

(2) Preparing the Unfired Heater

Using paste provided by wet mixing alumina powder with an organic binder, an organic solvent, etc., an unfired alumina sheet which will become a first alumina layer 122 was formed and as many through holes as the 32 elements were formed. Then, a predetermined pattern of conductive paste like that described above in (1) was printed at a predetermined place on one side of the unfired alumina sheet which will become the first alumina layer 122 and dried to form a heater element pattern which will become a heater element 121 and a lead part 1211 extending therefrom and an unfired conductor which will become through hole conductors 1221 and 1222. Using conductive paste like that described in (1) above, a predetermined terminal pattern which will become heater energization terminal pads 1241 and 1242 was printed at a predetermined place on the opposite side of the unfired alumina sheet which will become the first alumina layer 122 and dried. Next, an unfired alumina sheet which will become a second alumina layer 123 was prepared by a similar method as the first alumina layer 122 and was dried. Then, one side of the unfired alumina sheet which will become the second alumina layer 123 was laminated with the first alumina layer 122 on the side where the heater element pattern was printed, and layers 122 and 123 were pressed under reduced pressure. An unfired heater was thus prepared. Each unfired alumina sheet also has a size accommodating 32 first alumina layers 122 or 32 second alumina layers 123 for dicing, the pieces being separated by a predetermined spacing from one another.

(3) Forming an Unfired Laminated Sheet Body

The unfired sheet for the detection element prepared in (1) and the unfired heater prepared in (2) were laminated in such manner that the side of the unfired sheet for the detection element prepared in (1) (on which the electrode pattern which will become the reference electrode 113 and the lead part 1131 are formed) and the side of the unfired alumina sheet which will become the second alumina layer 123 opposite the unfired heater pattern prepared in (2) were facing each other. An unfired laminated sheet body was thus prepared.

(4) Print Process

A first porous layer paste for forming an unfired first porous layer which will become a part of the first porous layer 131 was screen-printed on the back of the unfired heater, of the tip containing the detection section of the unfired laminated sheet body formed in (3) (namely, the side opposite the heater element pattern of the unfired alumina sheet which will become the first alumina layer 122) and a coating film having a thickness of about 30 μm was formed. Then, the coating film was dried at 95° C. for two minutes. The first porous layer paste used for printing was prepared by blending 100 parts by mass of alumina powder, 15.5 parts by mass of polyvinyl butyral as an organic binder, 42 parts by mass of butyl carbitol as an organic solvent, and 65 parts by mass of carbon powder having a particle diameter of 5 to 20 μm as a porosity agent.

(5) Through Hole Forming Process

Figure 4:
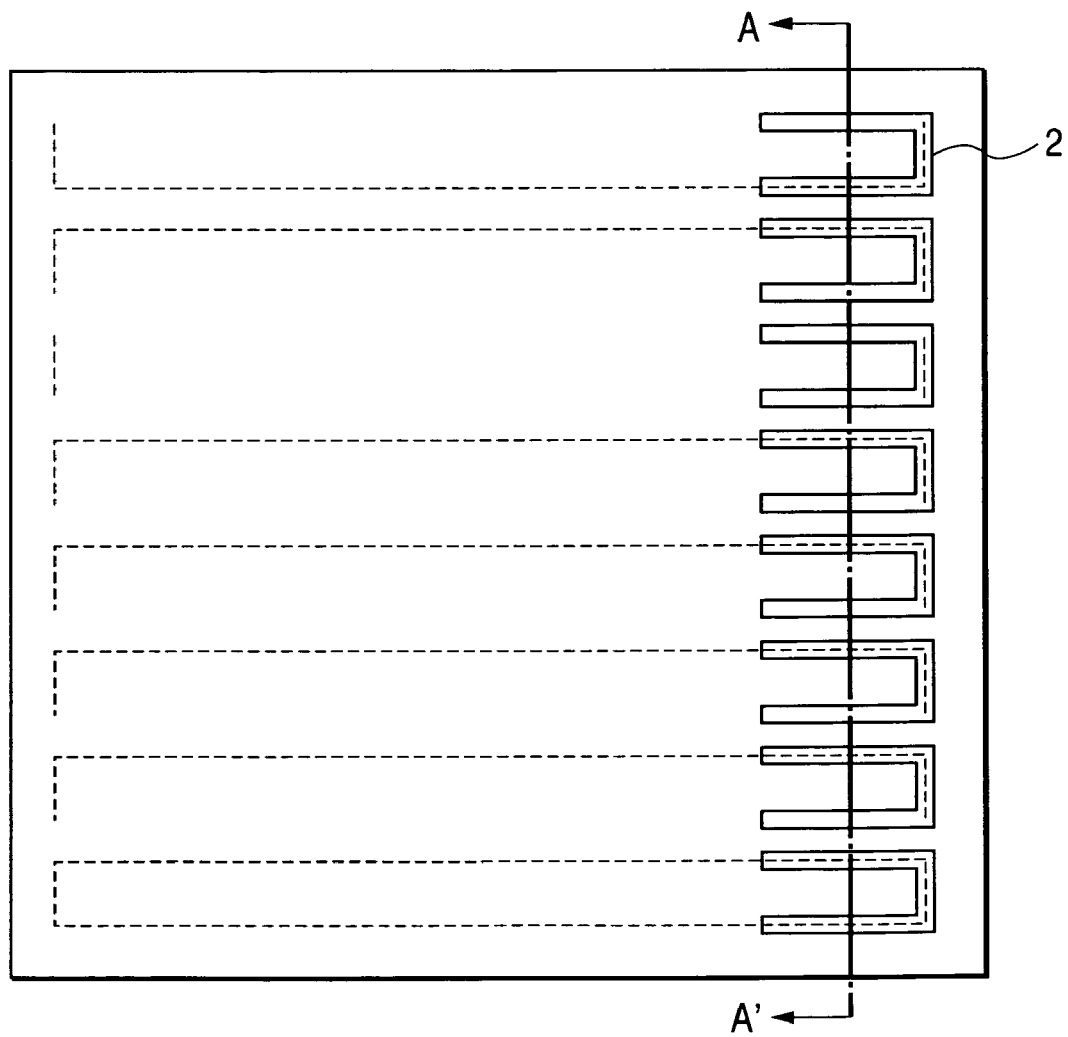
FIG. 4 is a plan view showing positions of through holes formed in an unfired sheet laminated body.
Figure 5:
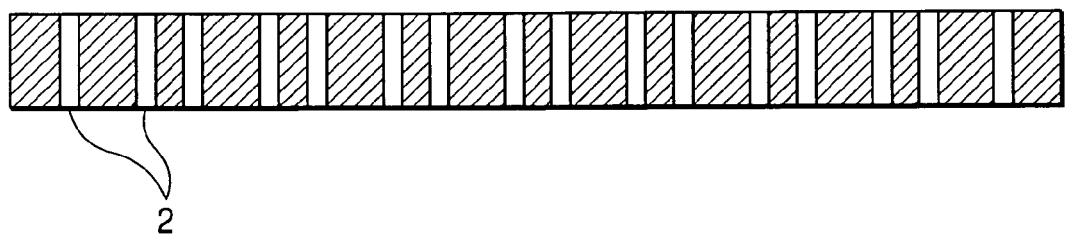
FIG. 5 is a sectional view taken along line A-A' in FIG. 4.

The unfired laminated sheet body was formed with through holes 2 each having a plane shape roughly like an angular U and having a width of 500 μm, as shown in FIGS. 4 and 5. Accordingly, the through holes 2 are formed at the same time in three sides of both sides and the tip side of the front portion 101 containing the part of the unfired sheet laminated body forming the detection section. That is, the through hole 2 is formed along the laminating direction of the unfired laminated sheet body, whereby the part forming the through hole 2 forms the narrow front portion 101. One unfired laminated sheet body was formed with as many through holes 2 as 32 elements by punching. The through hole 2 having a width of 500 μm was formed with a part straddling the allowance between pieces of the unfired laminated sheet body (in FIG. 4, each part surrounded by the dashed line indicates the size of each unfired element to be diced in the process described below).

(6) Filling Process

Figure 6:
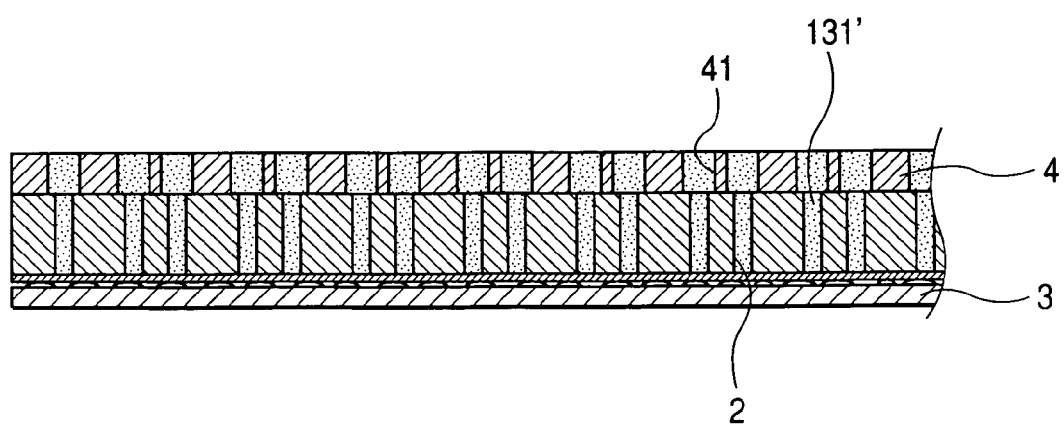
FIG. 6 is a schematic drawing which describes a filling process.
Figure 7:
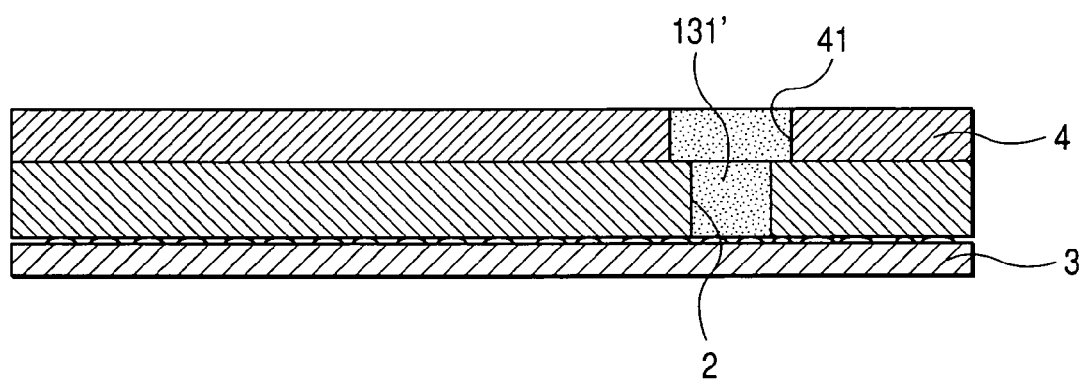
FIG. 7 is a sectional view showing parts of a through hole, a mold release agent, etc., of the unfired laminated sheet body of FIG. 6 on an enlarged scale.
Figure 8:
FIG. 8 is a schematic drawing (sectional view) which describes the structure of the mold release agent.

Each through hole 2 was filled with the first porous layer paste to form an unfired first porous layer 131' with a squeegee in a state in which a mold release agent 3 was placed on the lower face of the unfired laminated sheet body and a mask 4 was arranged on the top face, as shown in FIGS. 6 and 7. Then, the filled paste was dried at 60° C. for 180 minutes. The first porous layer paste used for filling is the same as the paste used in Print process (4) described above; it has viscosity such that it is easily filled into the through holes 2 and does not run after filling. A waterproof paper having pits and projections on the surface thereof with the difference in height between the pits and the projections being about 10 μm as shown in FIG. 8 was used as the mold release agent 3. A metal material having a thickness of 120 μm with each mask hole 41 having a width of 900 μm wider than the width of the through hole 2 (500 μm) by 400 μm was used as the mask 4. Accordingly, an unfired laminated sheet body filled with the unfired first porous layer 131' was prepared.

(7) Pressing of Unfired Sheet for Protection Layer and Unfired Sheet for Protective Insulating Layer Against Unfired Laminated Sheet Body An unfired sheet for protection layer which will become an electrode protection layer 116 was formed using a slurry provided by wet mixing predetermined amounts of alumina powder, carbon powder, a binder, an organic solvent, etc. Next, an unfired sheet for the protective insulating layer which will become a protective insulating layer 115 was formed using an unfired alumina sheet of the same composition as the unfired alumina sheet which will become the first alumina layer 122 and the second alumina layer 123. Then, the unfired sheet for the protective insulating layer was formed with an unfired conductor which will become through hole conductors 1151 and 1152 and a terminal pattern which will become signal output terminal pads 1141 and 1142. The unfired sheet for the protection layer and the unfired sheet for the protective insulating layer were appropriately laminated on the side of the unfired laminated sheet body after being subjected to the filling process in (6) above where the electrode pattern which will become the detection electrode 112 was formed, and the two unfired sheets were pressed under reduced pressure.

(8) Separating Process

Figure 9:
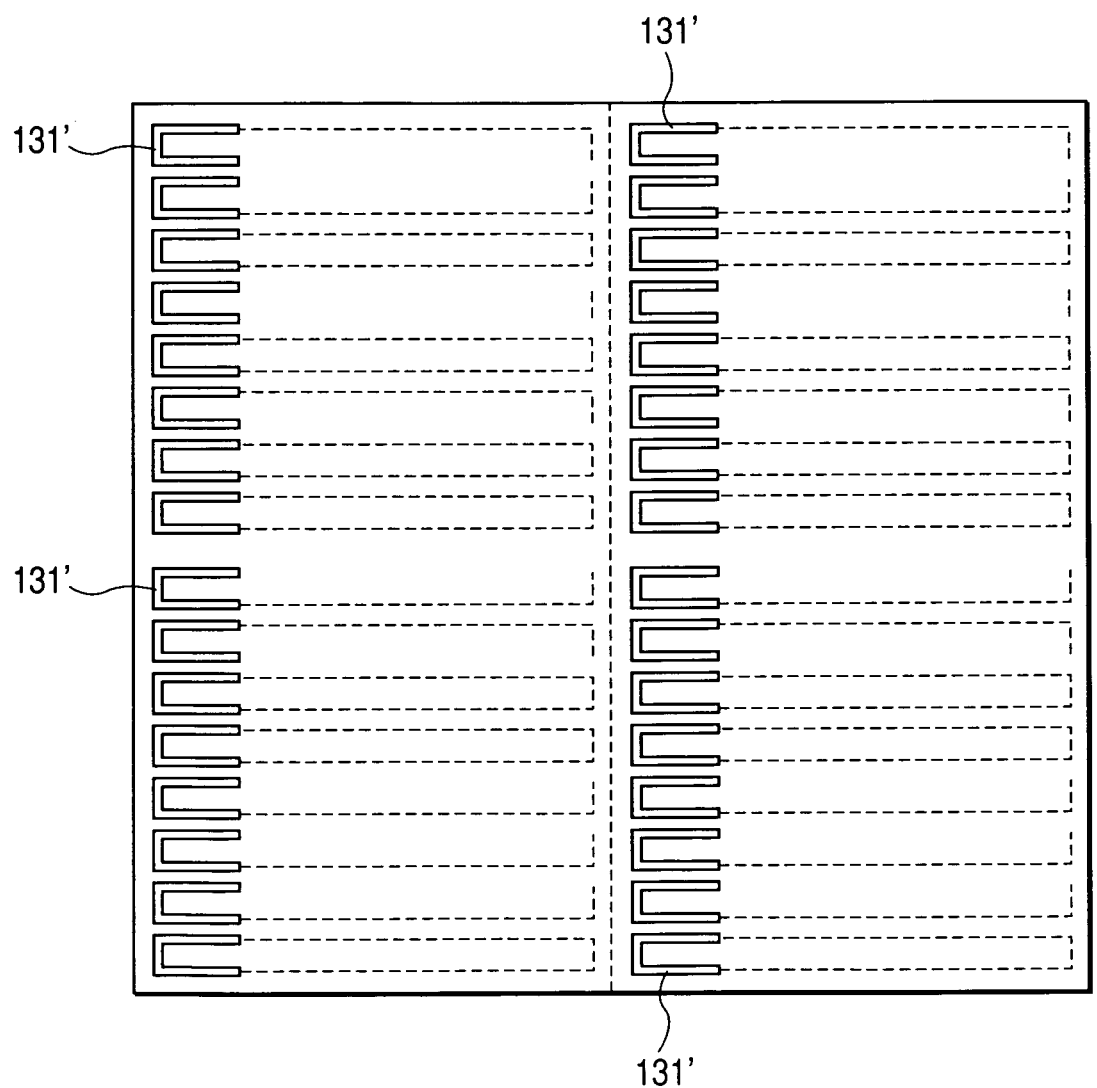
FIG. 9 is a plan view which schematically shows how one unfired laminated sheet body is formed with pieces which will be diced to form 32 unfired elements.

The laminated body shown in FIG. 9 having the through holes 2 filled with the first porous layer paste in (6) and having the unfired sheet for the protection layer and the unfired sheet for the protective insulating layer furthermore laminated on the unfired laminated sheet body in (7) was diced in sequence with a cutter along the dashed lines to provide a total of 32 unfired elements. The unfired elements were cut so as not to produce any step between the side face of the unfired laminated sheet body and the side face of the unfired first porous layer 131' made of the first porous layer paste. Each unfired element was diced so that the thickness of the unfired first porous layer 131' at both side edge faces of the front portion and at the tip edge face was 180 μm in the unfired element after dicing.

(9) Firing Process

Each unfired element provided in (8) was heated to 450° C. at a rate of 20° C./hour from room temperature in a degreasing furnace under ambient atmosphere, and was heat-treated at 450° C. for one hour for degreasing (de-binder treatment). Then, each unfired element was heated at a rate of 200° C./hour in the degreasing furnace and was fired for one hour at a maximum temperature of 1500° C. Upon firing, the porosity agent contained in the unfired first porous layer 131' was burned off and pores were produced to form a first porous layer 131.

(10) Forming Process of Second Porous Layer

Paste containing alumina powder, a binder (polyvinyl butyral), an organic solvent, and carbon powder as a porosity agent was printed on the entire peripheral area of the tip side containing the detection section of the element body formed with the first porous layer 131 so that the thickness of the porous protection layer 13 at the corner of the element body after firing will become 250 μm, and the paste was dried. Then, the element body in this state was heated at a rate of 10° C./hour under ambient atmosphere and was heat treated for one hour at a maximum temperature 900° C. to form a second porous layer 132 and by extension a porous protection layer 13. Thus, a lamination-type gas sensor element 1 having a front portion 101 of the element body formed narrower than the rear portion, where the front portion 101 was covered with the porous protection layer 13, was obtained.

Modified Example

Figure 11:
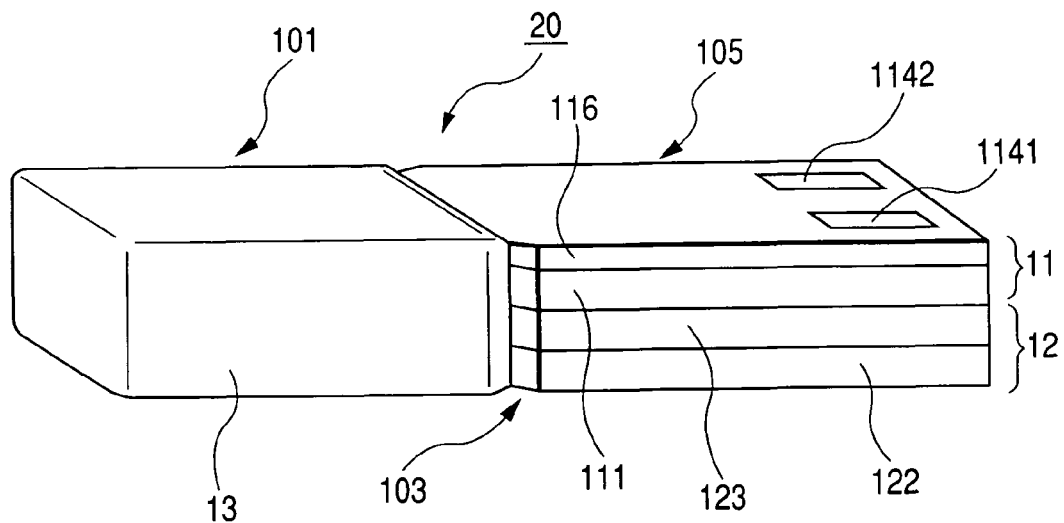
FIG. 11 is a perspective view schematically showing the appearance of a lamination-type gas sensor element of a modified example.

Next, a lamination-type gas sensor element 20 according to a modified example of the embodiment and a gas sensor 50 incorporating the lamination-type gas sensor element will be described with reference to FIGS. 11 to 13. FIG. 11 is a perspective view of the lamination-type gas sensor element 20 according to the modified example, and FIG. 12 is a plan view of the lamination-type gas sensor element 20 (plan view from the top of FIG. 11).

The lamination-type gas sensor element 20 according to the modified example differs largely from the lamination-type gas sensor element 1 of the embodiment described above in that in the element body having a detection element 11 and a ceramic heater 12 laminated on each other, an intermediate part 103 whose width increases gradually from a front portion 101 to a rear portion 105 is arranged between the front portion 101 containing a detection section and the rear portion 105 formed with signal output terminal pads 1141 and 1142 and heater energization terminal pads (not shown). Also, a porous protection layer 13 covers the sensor element 20 from its tip edge up to a boundary part 107 joining the side edge face of the intermediate part 103 along the laminating direction and the side edge face of the front portion 101 in addition to both side edge faces of the front portion 101. Therefore, parts of the lamination-type gas sensor element 20 according to the modified example similar to those of the lamination-type gas sensor element 1 of the embodiment described above will not be described again.

The lamination-type gas sensor element 20 according to the modified example has an element body having the detection element 11 and the ceramic heater 12 laminated on each other, and has the intermediate part 103 whose width increases gradually from the front portion 101 to the rear portion 105 between the front portion 101 and the rear portion 105, as described above. As shown in FIGS. 11 and 12, of both side edge faces along the laminating direction of the element body of the lamination-type gas sensor element 20, the porous protection layer 13 is formed from the tip end of the front portion 101 to a midway position of the intermediate part 103. The porous protection layer 13 has a two-layer structure comprising a first porous layer 131 and a second porous layer 132 as in the embodiment. In addition to what is shown in FIG. 12, the porous protection layer 13 is also formed on the right side and the back and the tip edge face of the element body. Thus, when a cross section of the lamination-type gas sensor element 20 is taken along the laminating direction of the front portion 101 containing the detection section, a cross section similar to the cross-sectional structure in the embodiment shown in FIG. 2 is obtained. In the modified example, however, a total dimension C of the width of the front portion 101 of the element body and the thickness of the porous protection layer 13 covering both side edge faces of the front portion 101 is smaller than the maximum width of the rear portion of the element body (namely, the width of a rear portion 105) D, as shown in FIG. 12.

Figure 12:
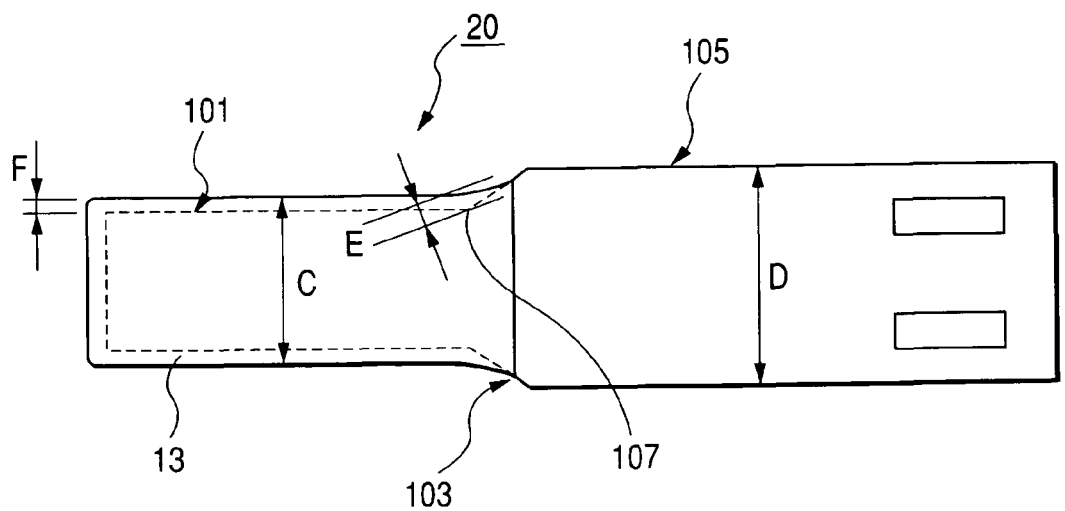
FIG. 12 is a plan view of the lamination-type gas sensor element of the modified example viewed from the detection element side.
Figure 13:
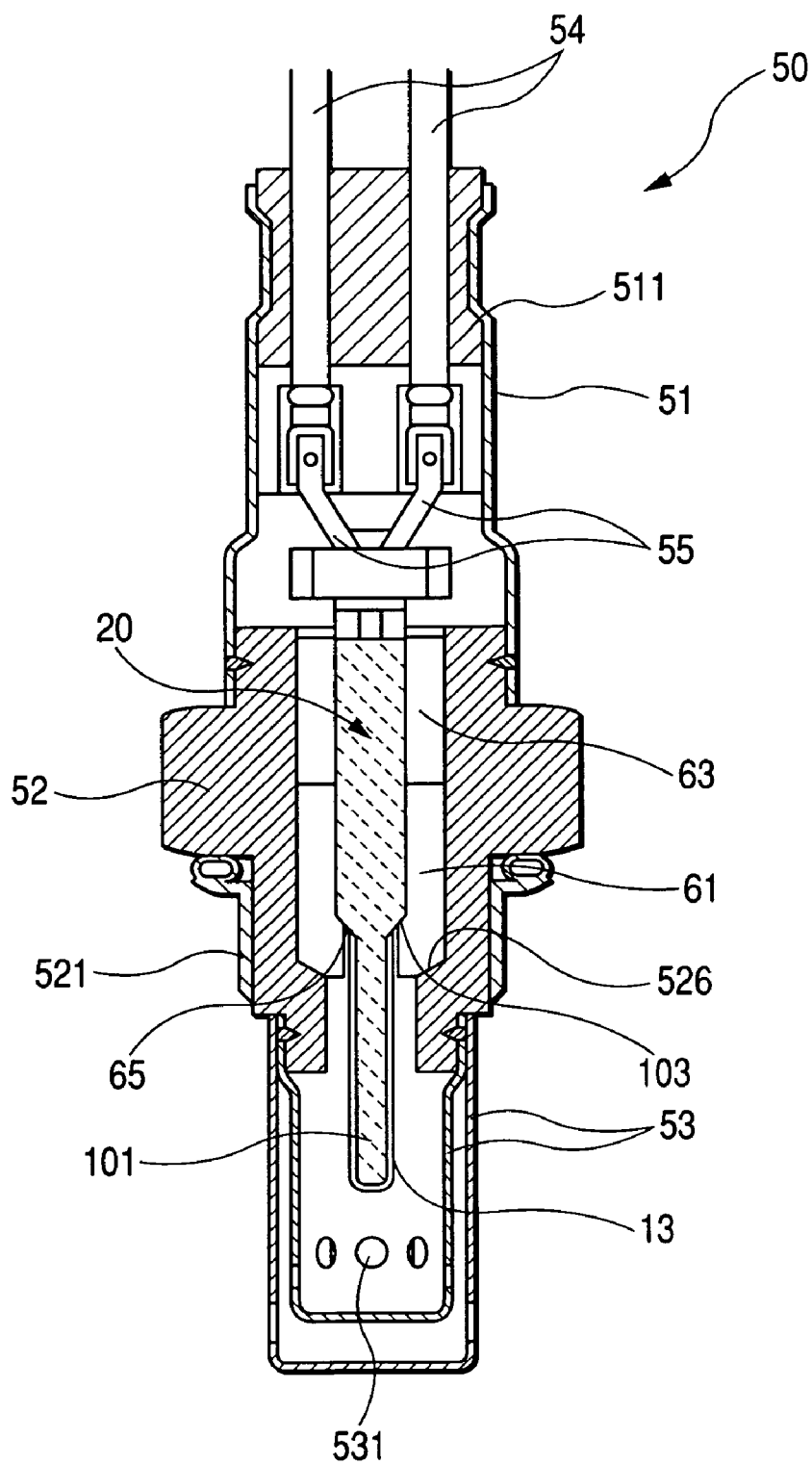
FIG. 13 is a general schematic sectional view showing the structure of the gas sensor (oxygen sensor) of the modified example.

The lamination-type gas sensor element 20 according to the modified example has a porous protection layer 13 covering the boundary part 107 joining the side edge face of the front portion 101 of the element body and the side edge face of the intermediate part 103 (see FIG. 12). In the porous protection layer 13, the thickness E at the boundary part 107 is larger than the thickness F at a side edge face of the front portion 101.

The lamination-type gas sensor element 20 according to the modified example can be prepared using a manufacturing process similar to that of the lamination-type gas sensor element 1 according to the embodiment described above. However, the through hole shape in (6) Through hole forming process, the cut pattern in (8) Separating process, and the like are changed appropriately so as to conform with the lamination-type gas sensor element 20 according to the modified example. When the lamination-type gas sensor element 20 according to the modified example is manufactured, (10) Forming process of second porous layer is changed appropriately so that the total dimension C of the width of the front portion 101 of the element body and the thickness of the porous protection layer 13 is less than the width D of the rear portion 105 of the element body. Specifically, in the forming process of second porous layer, the thickness of the paste forming a second porous layer 132 is previously adjusted (for application) or appropriate grinding is performed after the second porous layer is formed, thereby appropriately adjusting the thickness of the porous protection layer 13.

Next, a gas sensor 50 incorporating the lamination-type gas sensor element 20 according to the modified example will be described. In the gas sensor 50 according to the modified example, both side faces of the intermediate part 103 of the element body in the lamination-type gas sensor element 20 are engaged in a holder side engagement part 65 of a ceramic holder 61 installed in a housing 52, whereby the lamination-type gas sensor element 20 is positioned on the inside of the ceramic holder 61, as shown in FIG. 13. The ceramic holder 61 is engaged in a housing side engagement part 526 of the housing 52, whereby the lamination-type gas sensor element 20 is positioned inside the housing so that the front portion 101 containing the detection section protrudes from the housing. That is, in the gas sensor 50 of the modified example, the lamination-type gas sensor element 20 is positioned using the ceramic holder 61 unlike the gas sensor 5 of the embodiment wherein the lamination-type gas sensor element 1 is held at the predetermined position of the housing 52 as it is sealed with glass in the housing 52. A fill layer 63 consisting essentially of glass ceramics is provided at the rear of the ceramic holder 61 and inside the housing 52. The structures of an outer cylinder 51 and lead wires 54 are similar to those of the gas sensor 5 according to the embodiment.

In this manner, the gas sensor 50 according to the modified example adopts a structure where both side edge faces of the intermediate part 103 of the element body in the lamination-type gas sensor element 20 are engaged in the holder side engagement part 65 as described above. Thus, while the porous protection layer 13 in the lamination-type gas sensor element 20 covers the boundary part 107 joining the side edge face of the front portion 101 of the element body and the side face of the intermediate part 103, the porous protection layer 13 is formed so as to be apart from the holder side engagement part 65. This means that a portion not covered with the porous protection layer 13 on both side edge faces of the intermediate part 103 of the element body in the lamination-type gas sensor element 20 is engaged in the holder side engagement part 65 of the ceramic holder 61. As the porous protection layer 13 on both side edge faces of the intermediate part 103 of the element body does not overlap with the holder side engagement part 65, the outer face of the lamination-type gas sensor element 20 and the inner face of the ceramic holder 61 (the inner face of the holder side engagement part 65) can be brought into intimate contact with each other. Thus, entry of exhaust gas and water drops in the housing 51 through the inside of the porous protection layer 13 can be reliably suppressed, providing a highly reliable gas sensor 50.

Although the invention has been described according to the above embodiment and the modified example, it is to be understood that the invention is not limited to these specific embodiments, and that changes and modifications may be made appropriately without departing from the spirit and scope of the invention.

For example, in the embodiment described above, the oxygen sensor and the lamination-type gas sensor element for use with the oxygen sensor are described, but the invention can also be applied to gas sensors other than an oxygen sensor, such as a carbon monoxide sensor or an NOx sensor, and a lamination-type gas sensor element for use with such gas sensors.

In the embodiment described above, the lamination-type gas sensor element is formed with first and second porous layers, but may be formed with only a first porous layer. Further, to form the second porous layer, in the embodiment described above, while paste which will become the second porous layer is used, heat treatment is conducted for forming the second porous layer. However, the second porous layer may be formed by thermal spraying of the entire peripheral area of one end part of the element body formed with the first porous layer.

This application is based on Japanese Patent Application No. 2005-171754, filed Jun. 10, 2005 and Japanese Patent Application No. 2004-3502, filed Jan. 8, 2004, the entire contents of which are hereby incorporated by reference, the same as if set forth at length.

What is claimed is:

1. A gas sensor element comprising an element body having a front portion including two side faces and a rear portion, the element body including: a ceramic heater comprising ceramic layers and a heater element embedded in said ceramic layers; and a solid electrolyte layer comprising a detection section, the detection section being covered by a pair of electrodes, and the solid electrolyte layer being laminated with said ceramic heater, wherein the front portion of the element body including the detection section has a smaller width than the rear portion of the element body, and at least both side faces of the front portion of said element body are covered with a porous layer, said rear portion including a plurality of terminal electrodes on an outer surface thereof, the terminal electrodes being electrically connected to said pair of electrodes and said heater element, the element body further includes an intermediate part having opposed side faces provided between said front portion and said rear portion, said intermediate part including an engagement portion and having a width which gradually increases along a length of the element body from the front portion to the rear portion, and said porous layer covers a side edge face of a boundary part between said front part and said intermediate part, and the porous layer extends from a tip end of the front portion of the element body to a midway position of the intermediate part so that the engagement portion as well as the rear portion of the element body are not covered by the porous layer, said porous layer being set apart from the engagement portion.

2. The gas sensor element as claimed in claim 1, wherein the porous layer provided on the side face of said boundary part is thicker than the porous layer provided on the side face of the front portion.

3. The gas sensor element as claimed in claim 1, wherein a total dimension of the width of the front portion of the element body and a thickness of the porous layer provided on both side faces of the front portion is equal to or smaller than a maximum width of the rear portion of the element body.

4. The gas sensor element as claimed in claim 1, satisfying a relationship of A×0.60<B<A×0.98 where A is the width (mm) of the front portion of said element body and B is a maximum width (mm) of a part of said heater element provided in said front portion.

5. The gas sensor element as claimed in claim 1, wherein said porous layer covers the periphery of said front portion, said porous layer including a first porous layer covering at least both side faces of the front portion of the element body and a second porous layer covering the first porous layer.

6. The gas sensor element as claimed in claim 1, wherein said porous layer covers the periphery of said front portion, including both side faces of the front portion, and the porous layer at a corner of said element body has a thickness of 20 µm or more.

7. The gas sensor element as claimed in claim 1, wherein said porous layer has a porosity of from 15% to 65%.

8. A gas sensor comprising:
a gas sensor element as claimed in claim 1; and
a cylindrical housing including a tip end surrounding said gas sensor element, said detection section protruding from the tip end of said housing.

9. A gas sensor comprising:
a gas sensor element as claimed in claim 1;
a cylindrical housing including a tip end surrounding said gas sensor element, said detection section protruding from the tip end of said housing;
an insulating ceramic holder provided between said gas sensor element and said housing, said insulating ceramic holder comprising an engagement part; wherein
the opposed side faces in a rear portion of said intermediate part are engaged in the engagement part of said insulating ceramic holder, apart from a rear end of the porous layer.

* * * * *